United States Patent
Hancock et al.

(10) Patent No.: US 7,598,745 B2
(45) Date of Patent: Oct. 6, 2009

(54) METHOD AND APPARATUS FOR MEASURING ELECTRICAL CONDUCTIVITY

(75) Inventors: Nigel Harold Hancock, Queensland (AU); Andrew Douglas Maxwell, Toowoomba (AU); Antonio Louis Ah Fock, Toowoomba (AU)

(73) Assignee: The University of Southern Queensland, Toowoomba, Queensland (AU)

( * ) Notice: Subject to any disclaimer, the term of this patent is extended or adjusted under 35 U.S.C. 154(b) by 485 days.

(21) Appl. No.: 10/586,460

(22) PCT Filed: Jan. 14, 2005

(86) PCT No.: PCT/AU2005/000040

§ 371 (c)(1),
(2), (4) Date: Jul. 14, 2006

(87) PCT Pub. No.: WO2005/069022

PCT Pub. Date: Jul. 28, 2005

(65) Prior Publication Data

US 2008/0211518 A1   Sep. 4, 2008

(30) Foreign Application Priority Data

Jan. 15, 2004   (AU) ............................... 2004900161
Jun. 21, 2004   (AU) ............................... 2004903333

(51) Int. Cl.
*G01N 27/02*   (2006.01)
(52) U.S. Cl. ...................... 324/445; 324/444; 324/439
(58) Field of Classification Search ................. 324/445, 324/444
See application file for complete search history.

(56) References Cited

U.S. PATENT DOCUMENTS

| | | | | |
|---|---|---|---|---|
| 3,510,761 | A * | 5/1970 | Brown | 324/445 |
| 4,138,639 | A * | 2/1979 | Hutchins | 324/442 |
| 5,341,102 | A | 8/1994 | Akiyama et al. | |
| 5,455,513 | A * | 10/1995 | Brown et al. | 324/445 |
| 5,793,214 | A * | 8/1998 | Wakamatsu | 324/601 |
| 6,414,493 | B1 * | 7/2002 | Rezvani | 324/442 |
| 6,812,709 | B2 * | 11/2004 | Wieland et al. | 324/445 |

FOREIGN PATENT DOCUMENTS

EP   483690   7/1995

OTHER PUBLICATIONS

Derwent Abstract Accession No. 88-104531/15 & SU 1337821, Sep. 15, 1987.
McPhillips, J. & Snow, N., "Studies on Milk with a New Type of Conductivity Cell," The Australian Journal of Dairy Technology, Oct.-Dec. 1958, pp. 192-196.
Gupta, S. & Hills, G., "A Precision Electrode-Less Conductance Cell for Use at Audio Frequencies," Journal of Scientific Instruments, vol. 33, Aug. 1956, pp. 313-314.

* cited by examiner

*Primary Examiner*—Timothy J Dole
*Assistant Examiner*—John Zhu
(74) *Attorney, Agent, or Firm*—Dilworth & Barrese LLP

(57) ABSTRACT

An apparatus (2) for measuring electrical conductivity in a material has a pair of electrically conducting elements (6), a first electrical conductor (9) coupled to the electrically conducting elements and coupling a first transformer core (10) and a second transformer core (12) to form a first current loop (8), and a second electrical conductor (17) of known resistance coupling the second transformer core (12) and a third transformer core (14) to form a second current loop (16).

20 Claims, 17 Drawing Sheets

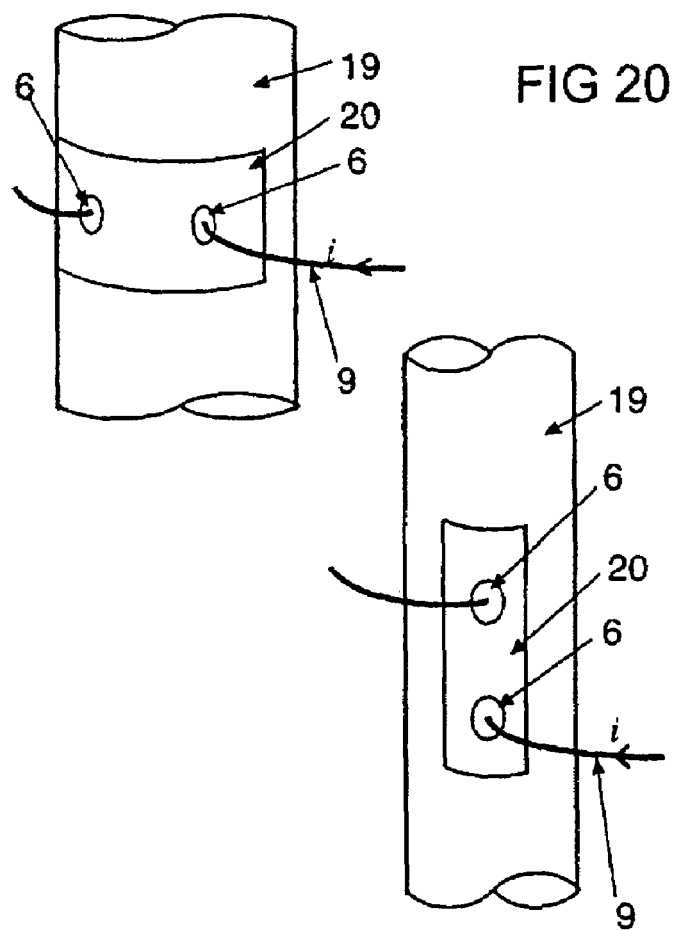
FIG 20
FIG 21
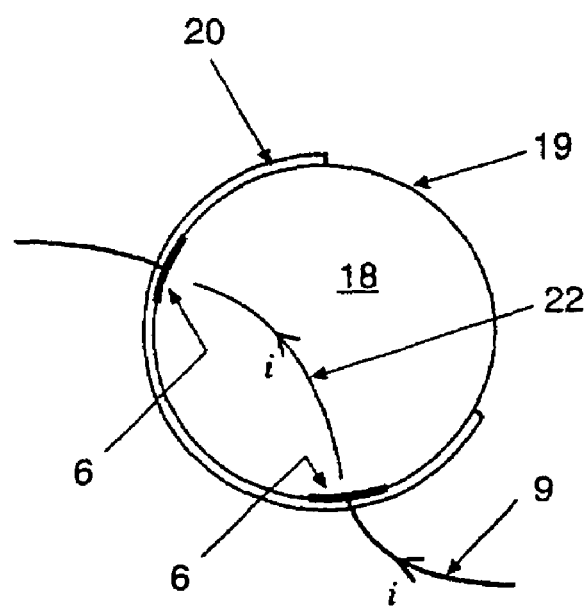
FIG 22

METHOD AND APPARATUS FOR MEASURING ELECTRICAL CONDUCTIVITY

FIELD OF THE INVENTION

The invention relates to a method and apparatus for the measurement of electrical conductivity and in particular the measurement thereof in materials having low electrical conductivity. In particular, although not exclusively, the invention relates to an apparatus and method for measuring electrical conductivity in low conductivity bulk materials. However, the method and apparatus of the present invention may also be employed with materials having high electrical conductivity.

BACKGROUND TO THE INVENTION

The ability to accurately measure electrical conductivity in bulk materials is required in many different fields and in particular this ability is required for measuring electrical conductivity in materials having a low electrical conductivity. One example is the food industry wherein electrical conductivity is measured to determine and/or investigate characteristics of foodstuffs. For example, techniques for measuring the electrical conductivity of milk have been employed to investigate both the physical chemistry of milk and the growth of bacteria therein.

McPhillips, J. & Snow, N. (1958), "Studies on Milk with a New Type of Conductivity Cell", The Australian Journal of Dairy Technology pp. 192-196 discloses an electrical arrangement for performing such measurements in relation to milk and Gupta, S. & Hills, G. (1956), "A Precision Electrode-less Conductance Cell for use at Audio Frequencies" discloses a similar electrical arrangement. Both arrangements comprise a current loop coupled between an energising circuit and a sensing circuit via two toroidal transformers.

However, these arrangements are unsuitable for various applications such as vat applications because the material being measured fouls and blocks the current loop, which further causes problems when the vat has to be cleaned.

Another problem with these arrangements is that they suffer from supply energisation fluctuations, which cause measurement noise and require stabilisation of the power supply and supply voltage monitoring.

Hence, there is a need for a system and/or method and/or apparatus for accurately measuring electrical conductivity that addresses or at least ameliorates the aforementioned problems. In particular, such a system, method and/or apparatus is required for measuring electrical conductivity in materials having a low electrical conductivity.

In this specification, the terms "comprises", "comprising" or similar terms are intended to mean a non-exclusive inclusion, such that a method, system or apparatus that comprises a list of elements does not include those elements solely, but may well include other elements not listed.

SUMMARY OF THE INVENTION

In one form, although it need not be the only or indeed the broadest form, the invention resides in an apparatus for measuring electrical conductivity in a material, said apparatus comprising:

a pair of electrically conducting elements for contacting the material;

a first electrical conductor coupled to said electrically conducting elements, said first electrical conductor coupling a first transformer core and a second transformer core to form a first current loop; and a second electrical conductor of known resistance coupling said second transformer core and a third transformer core to form a second current loop.

Suitably, said electrically conducting elements are in the form of bolts or plugs. Alternatively, said electrically conducting elements are in the form of plates or rings.

Suitably, said first, second and third transformer cores are in the form of toroidal "C", "O" or "E" transformer cores or combinations thereof.

Suitably, said first, second and third transformer cores are ferrite cores, laminated cores or powdered iron cores or combinations thereof.

Preferably, the apparatus further comprises at least one mounting plate to which said electrically conducting elements are attached, said at least one mounting plate attached to a container for said material.

Suitably, said second current loop is partially formed by a metal loop attached to said at least one mounting plate and electrically coupled to said electrically conducting elements, said metal loop supporting said first and second transformer cores.

According to one embodiment, said first, second and third transformer cores are in the form of toroidal "O" transformer cores coupled to said metal loop such that axes of the transformer cores are mutually perpendicular.

In another form, the invention resides in a method of measuring electrical conductivity in a material, said method including the steps of:

mounting a pair of electrically conducting elements to be in contact with said material;

coupling said pair of electrically conducting elements with a first electrical conductor, said first electrical conductor coupling a first transformer core and a second transformer core to form a first current loop;

coupling said second transformer core and a third transformer core with a second electrical conductor of known resistance to form a second current loop;

measuring a voltage across said material with said first transformer core;

monitoring an excitation voltage across said second transformer core by measuring a reference voltage across said third transformer core; and determining said electrical conductivity of said material from said voltage across said material, said reference voltage and said known resistance.

Alternatively, said electrical conductivity of said material is determined from current measurements corresponding to said voltage measurements.

Further features of the present invention will become apparent from the following detailed description.

BRIEF DESCRIPTION OF THE DRAWINGS

To assist in understanding the invention and to enable a person skilled in the art to put the invention into practical effect preferred embodiments of the invention will be described by way of example only with reference to the accompanying drawings, wherein:

FIG. 20 is a perspective view of an embodiment of the present invention applied to measuring electrical conductivity of materials in pipelines;

FIG. 21 is an alternative embodiment to that shown in FIG. 20;

FIG. 22 is a plan view of the embodiment shown in FIG. 20; and

DETAILED DESCRIPTION OF THE INVENTION

Figure 1:
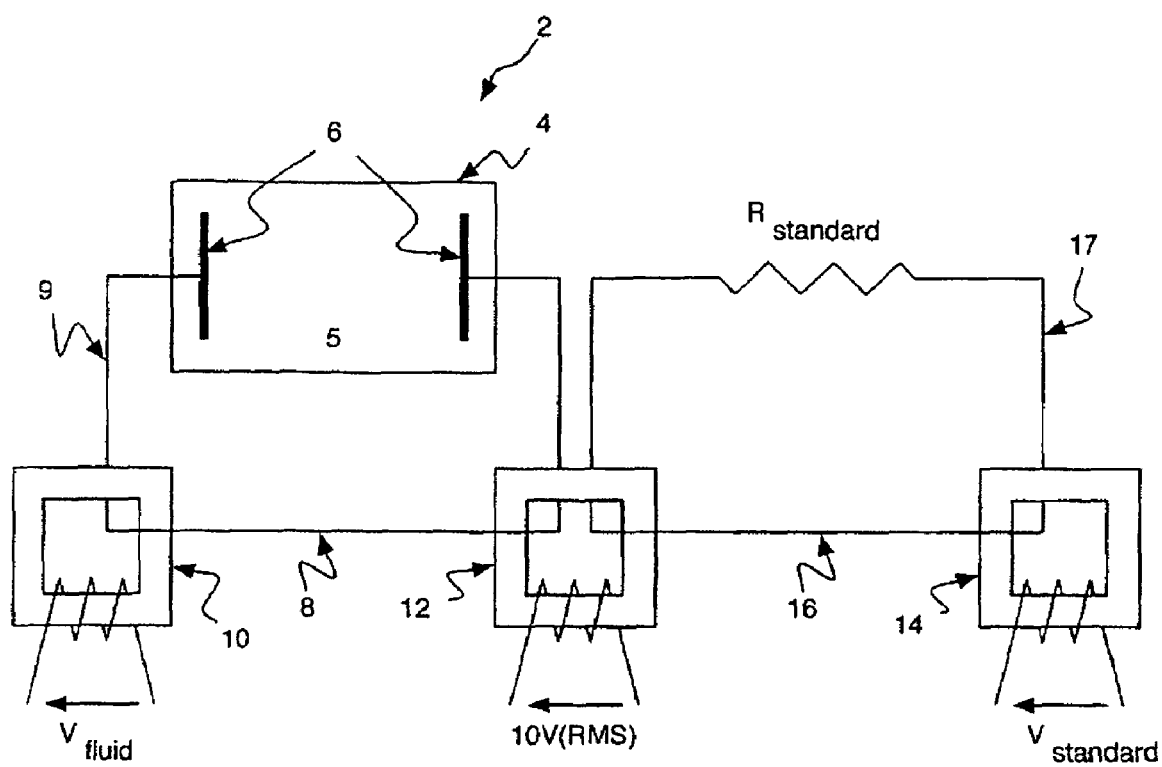
FIG. 1 is a schematic representation of an apparatus for measuring electrical conductivity in materials in accordance with an embodiment of the present invention.
Figure 2:
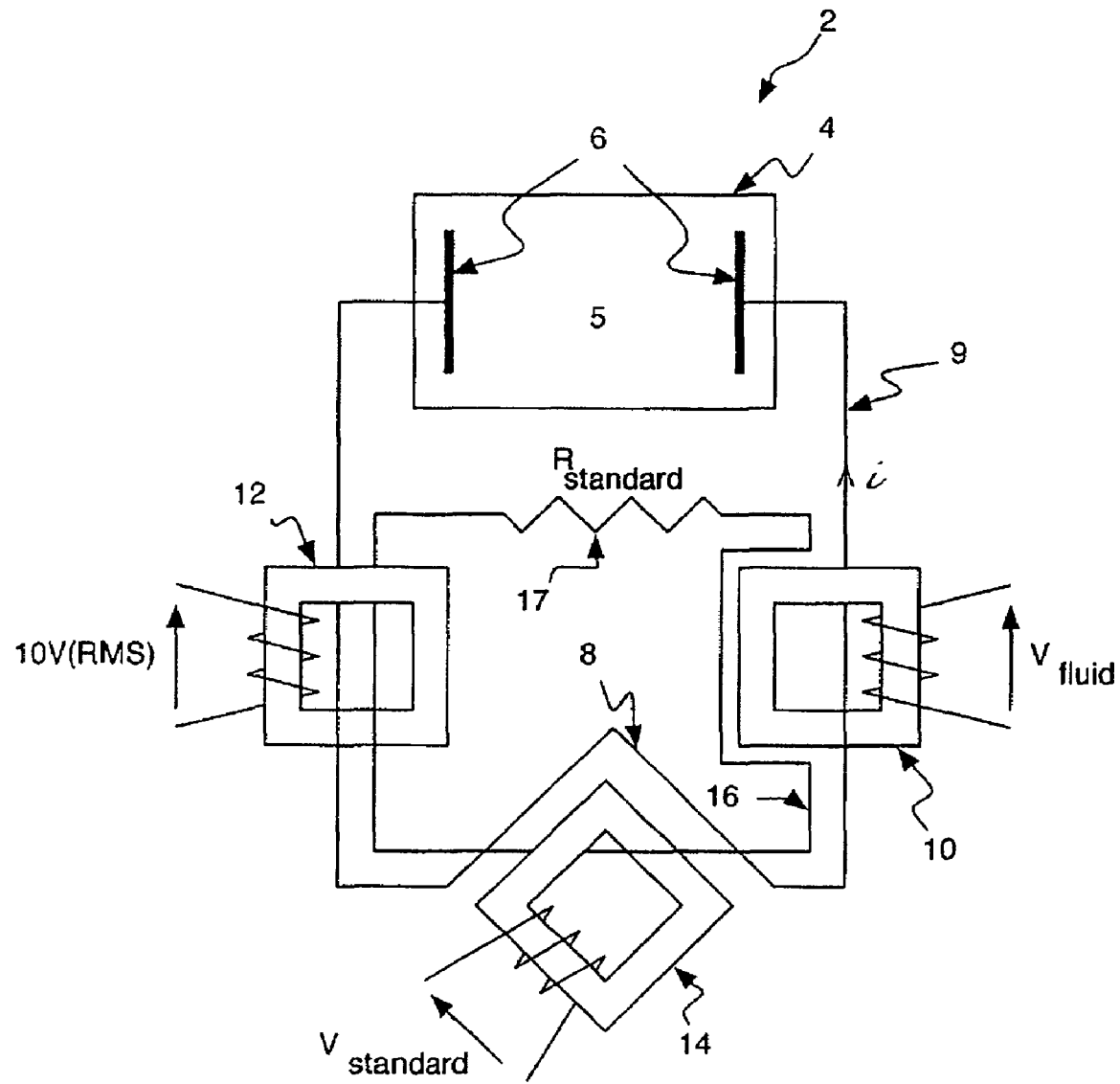
FIG. 2 is an alternative representation of the apparatus shown in FIG. 1 showing the physical arrangement of the components of the apparatus.

Referring to FIGS. 1 and 2, there is provided an apparatus 2 for accurately measuring electrical conductivity in materials and in particular for measuring electrical conductivity in bulk materials having a low electrical conductivity. Apparatus 2 comprises a container in the form of fluid cell 4 containing a material, which in this example is in the form of a fluid 5. Fluid cell 4 is configured in the same manner as a standard conductivity measurement cell and comprises a pair of electrically conducting elements in the form of a pair of plates 6 arranged to be in contact with the fluid 5. The construction of fluid cell 4 in this embodiment would be familiar to a person skilled in the art.

Apparatus 2 further comprises a first current loop 8 formed by a first electrical conductor in the form of a first wire 9 passing through a first transformer core 10 and through a second transformer core 12. A third transformer core 14 is provided for reference monitoring and a second current loop 16 is formed by a second electrical conductor in the form of a second wire 17 passing through second transformer core 12 and third transformer core 14. In one embodiment, transformer cores 10, 12, 14 are in the form of toroidal ferrite "C" transformer cores, but alternative transformer cores may be employed such as toroidal ferrite "O" or "E" transformer cores. Combinations of the toroidal ferrite "C", "O" and/or "E" transformer cores may be employed. In alternative embodiments, laminated transformer cores or powdered iron transformer cores may be employed. However, the Applicant has identified that toroidal ferrite "O" transformer cores are preferred due to their improved electromagnetic stability and self-shielding properties, which promote improved dynamic range of the instrumentation of the method and apparatus.

First transformer core 10 measures the voltage, $V_{fluid}$, across the fluid 5 of the fluid cell 4 and second transformer core 12 is an energising core with a typical excitation voltage of 10V RMS. Second wire 17 forming second current loop 16 has a known resistance $R_{standard}$ and second current loop 16 couples both the second transformer core 12 and third transformer core 14, but not the first transformer core 10, which is for measuring the voltage, $V_{fluid}$, across the fluid 5 of the fluid cell 4. The sensed voltages depend on the excitation voltage across the second transformer core 12 and the addition of the third transformer core 14 allows for inherent monitoring of the excitation voltage, which enables the aforementioned prior art noise and stability problems to at least be minimised.

The resistance $R_{fluid}$ of the fluid 5 between plates 6 in fluid cell 4 is expressed in equation 1:

$$R_{fluid} = (R_{standard} \times V_{fluid})/V_{standard} \qquad \text{Eqn. (1)}$$

The resistance $R_{fluid}$ of the fluid is proportional to its resistivity $\rho_{fluid}$ and the conductivity $\sigma_{fluid}$ of the fluid is the reciprocal of the resistivity. Hence, the conductivity $\sigma_{fluid}$ of the fluid is proportional to the reciprocal of the resistance $R_{fluid}$ of the fluid.

The Applicant has identified that the arrangement of the apparatus shown in FIGS. 1 and 2 presents some difficulties when implementing in large, vat style structures. Therefore, the Applicant has devised an alternative apparatus for practical implementation, as shown in another embodiment of the present invention in FIG. 3. Like reference numerals are used for like features between embodiments.

In this embodiment, the container for the material being measured, which replaces fluid cell 4 of the previous embodiments, is in the form of a vat 18 having vat walls 19. Plates 6 are made from suitable food grade stainless steel, identical to that used for vat 18 to avoid the generation of thermocouple effects. In the embodiment shown in FIG. 3, plates 6 are mounted on a mounting plate 20, which, in this embodiment, is made of PTFE. However, any other suitable food grade plastic may be employed. It will be appreciated that this arrangement allows the apparatus 2 to be mounted to vat walls and other containers holding the material being measured. This arrangement creates a "half-current loop" 22 between plates 6, thus enabling non-galvanic conductivity measurement. Mounting plate 20 insulates plates 6 from each other and from vat walls 19.

The mechanical implementation of the apparatus will now be described with reference to FIGS. 4-6.

Figure 4:
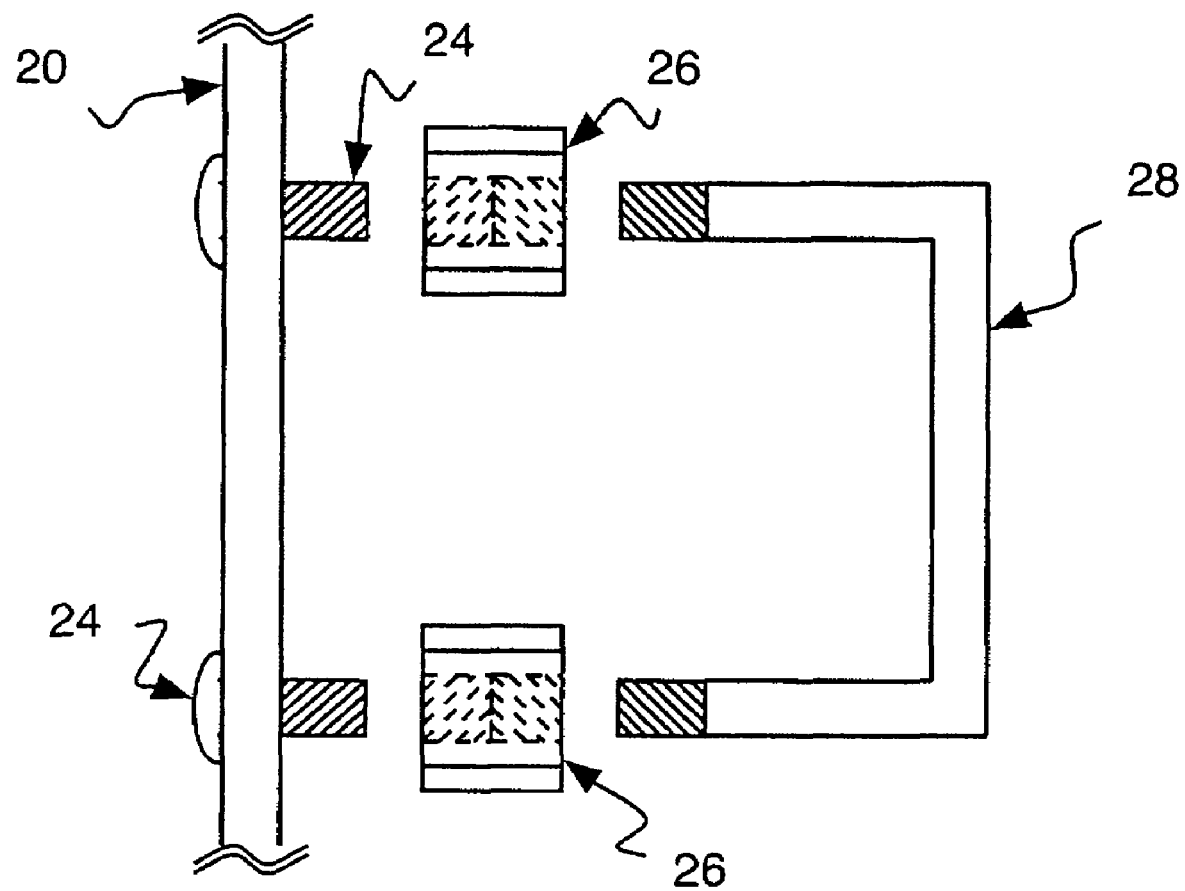
FIG. 4 is a plan view of a mounting plate, fastening means and half-current loop.
Figure 5:
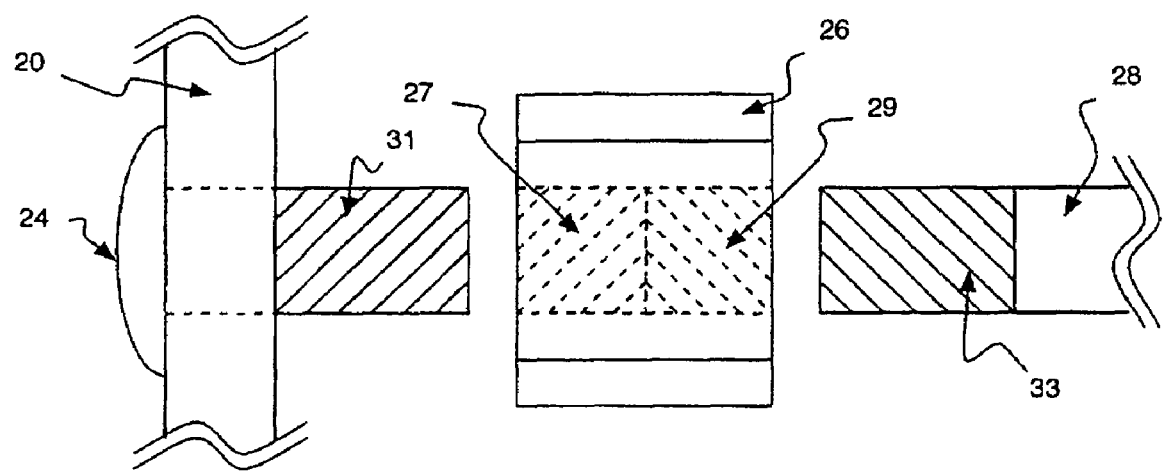
FIG. 5 in an enlargement of part of FIG. 4.

Referring to FIG. 4, a metal loop 28 is attached to mounting plate 20 by fastening means to create the aforementioned half-current loop 22. In this embodiment, the fastening means are in the form of a pair of bolts 24 and a pair of nuts 26. Alternatively, specially manufactured plugs may be employed or other suitable known fastening means. The enlargement shown in FIG. 5 shows that each nut 26 comprises a first thread 27 arranged in a first direction, e.g. clockwise and a second thread 29 arranged in the opposite direction, i.e. counter-clockwise in this example. The direction of the threads 31 of the bolts 24 and the direction of the threads 33 on the ends of the metal loop 28 are arranged in this manner to allow the nuts 26 to be securely attached to the bolts 24 and the ends of the metal loop 28 to be attached to the nuts 26, thus producing a secure electrical join. The ends of the bolts 24 and the loop 28 are designed such that they bite into each other to minimise electrical losses through the join between the bolts 24 and the metal loop 28.

The reliable connection of low and preferably zero electrical resistance between the bolts 24 and the loop 28 may be achieved in a number of ways. For example, threads 31, 33 may be milled to have a pattern of raised teeth or other such small, sharp raised sections that are crushed by tightening of nut 26. Alternatively, ends of the bolt 24 and loop 28 may be complimentarily shaped, such as cone shaped and inverse cone shape, such that they mate into each other to produce a good conductive join. A further alternative could be to use a layer of material such as beryllium comprising the small, sharp raised sections referred to above on both surfaces. The layer is then inserted between the ends of the threads 31, 33 to provide the desired biting effect. Beryllium has good biting properties and is commonly used for such purposes, but may have the drawback of producing undesirable thermocouple effects.

Preferably, bolts 24, nuts 26 and metal loop 28 are made from identical grade stainless steel to avoid the generation of any thermal e.m.f. The appropriate food grade of stainless steel is used, which is safe and suitable for food process industry applications. The use of such stainless steel also prevents contamination of food substances and the like that can occur when other materials such as copper are employed, which have associated problems such as copper creep and grain boundary diffusion.

Optionally, additional support for the loop 28 may be provided to minimise the mechanical load exerted on the bolts 24 and mounting plate 20. Such additional support may be in the form of bracing, bridging, welding or other form of support known in the art providing it is fully insulating to avoid interference with the current loop 28. Suitable plastic materials, PTFE or stainless steel insulated at the points of contact with loop 28 may be employed for such purpose.

Figure 6:
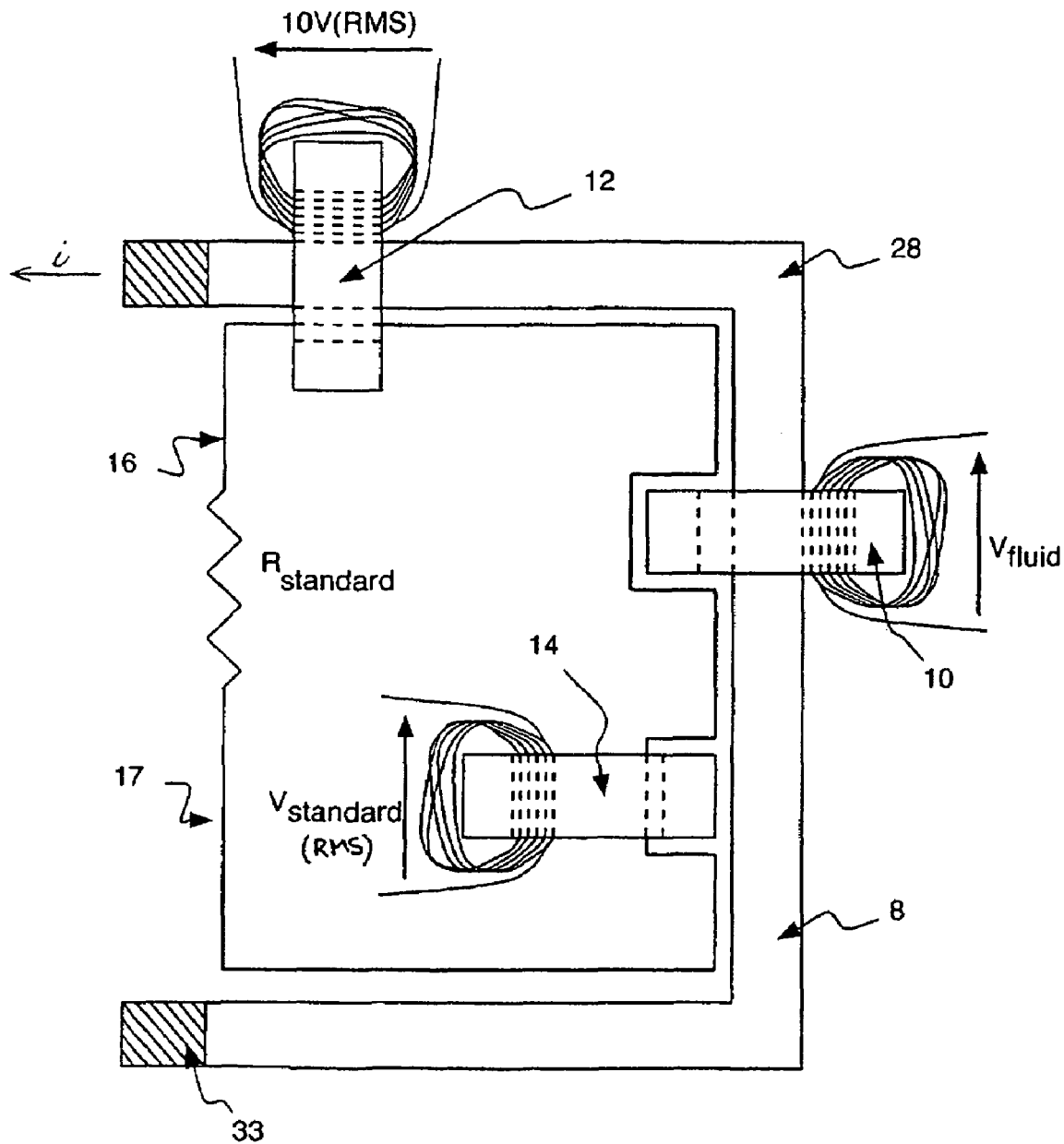
FIG. 6 shows first, second and third transformer cores, the first current loop and the half-current loop.

With reference to FIG. 6, first and second transformer cores 10, 12 are mounted on the loop 28, which forms part of the first current loop 8. Third transformer core 14 is not supported by loop 28, but is maintained in position by any suitable form of insulated support, such as plastic, PTFE or stainless steel insulated at the points of contact. Wire 17 of known resistance couples second transformer core 12 and third transformer core 14 forming second current loop 16 as shown.

The first, second and third transformer cores have x, y and z windings respectively, where the approximate values and ranges for x, y and z are as follows: x=100-200; y=20; z=100-200. The number of windings employed depends on the dimensions and magnetic properties of the cores 10, 12, 14, the selected range of inter-electrode resistance to be measured and the desired voltage output levels. As the number of windings on the cores increases, so does the sensitivity of the apparatus 2. However, increasing the number of windings also increases the capacitance, resistance and inductance and thus affects the low pass filtering and coil harmonics parameters.

The testing of the apparatus and the method of the present invention will now be described with reference to FIGS. 3, 6-8 and Table 1 herein.

Figure 3:
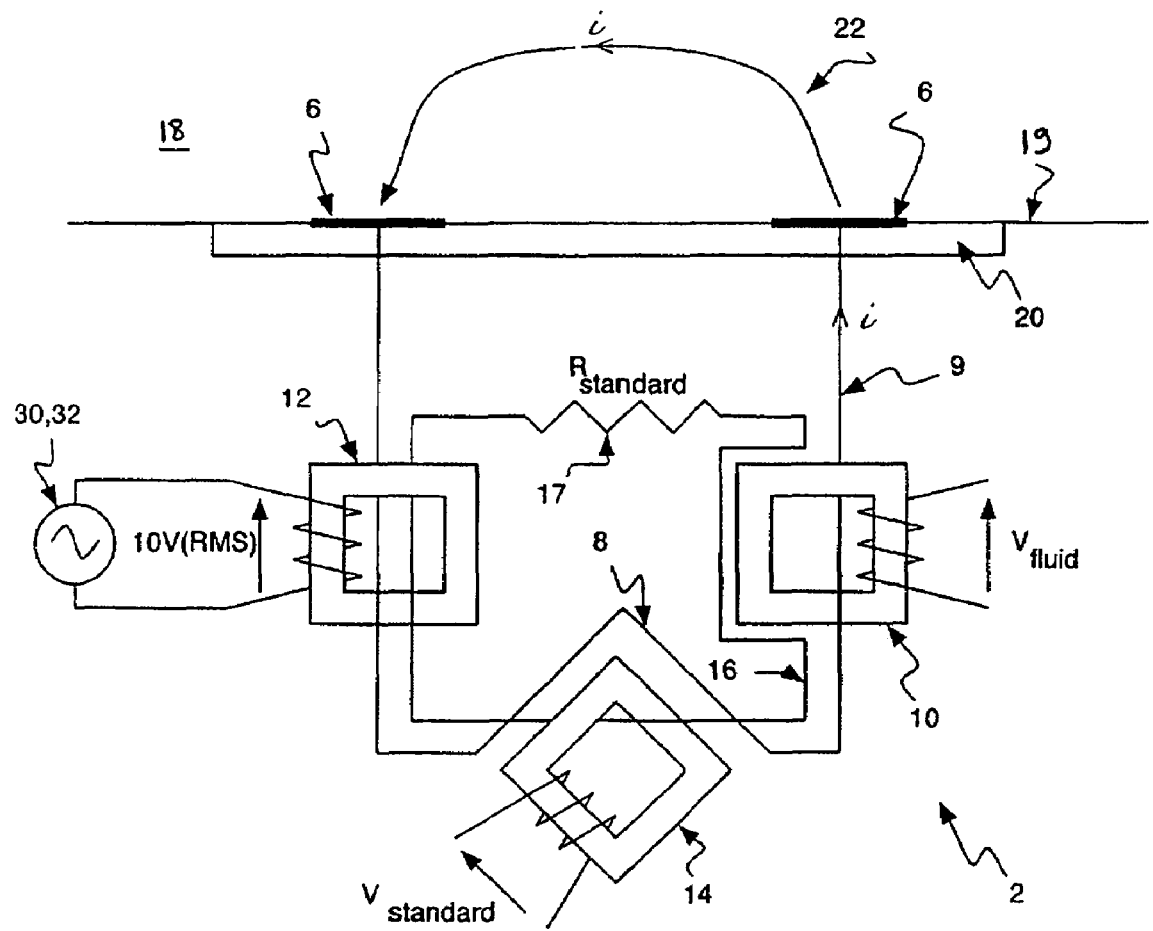
FIG. 3 is a schematic representation of a second embodiment of the apparatus of FIGS. 1 and 2.

Referring to FIGS. 3 and 6, a sinusoidal signal of 30 kHz generated by a precision frequency signal generator 30 is amplified by a high power amplifier 32 and the amplified signal is input to the second transformer core 12. The voltage ratio $V_{ratio}$ from equation 1 of the fluid voltage $V_{fluid}$ and the voltage $V_{standard}$ across the third transformer core 14 is expressed in equation 2;

$$V_{ratio} = V_{fluid}/V_{standard} \qquad \text{Eqn. (2)}$$

In this embodiment, fluid cell 4 had a capacity of 10 L and was filled with potassium chloride (KCl) solution. The molarity of the KCl solution was varied in a predetermined and repeatable fashion by adding KCl salt in predetermined quantities. For the solution of each molarity, $V_{fluid}$ and $V_{standard}$ were measured and the results are shown in Table 1:

TABLE 1

| KCl Molarity [M] | Measured Vref [V] | Measured Vfluid [V] | Theoretical Conductivity [mS/cm] | Measured Ratio Vfluid/Vref | Theoretical Corrected Ratio (1 + 1.75 * Molarity) * Ratio |
|---|---|---|---|---|---|
| 0 | 1.760 | 0.025 | 0.119 | 0.014 | 0.014 |
| 0.01 | 1.755 | 0.692 | 1.408 | 0.395 | 0.401 |
| 0.02 | 1.757 | 1.318 | 2.694 | 0.750 | 0.776 |
| 0.03 | 1.787 | 1.929 | 3.976 | 1.079 | 1.136 |
| 0.04 | 1.795 | 2.495 | 5.254 | 1.390 | 1.487 |
| 0.05 | 1.798 | 3.049 | 6.529 | 1.696 | 1.844 |
| 0.06 | 1.798 | 3.577 | 7.800 | 1.989 | 2.198 |
| 0.07 | 1.802 | 4.080 | 9.068 | 2.264 | 2.542 |
| 0.08 | 1.802 | 4.558 | 10.332 | 2.529 | 2.884 |
| 0.09 | 1.802 | 5.030 | 11.593 | 2.791 | 3.231 |
| 0.1 | 1.803 | 5.544 | 12.850 | 3.075 | 3.613 |
| 0.2 | 1.812 | 9.388 | 25.223 | 5.181 | 6.994 |
| 0.3 | 1.819 | 12.389 | 37.237 | 6.811 | 10.387 |
| 0.4 | 1.825 | 14.797 | 48.893 | 8.108 | 13.784 |
| 0.5 | 1.829 | 16.798 | 60.190 | 9.184 | 17.220 |
| 0.6 | 1.833 | 18.472 | 71.129 | 10.077 | 20.659 |
| 0.7 | 1.833 | 20.090 | 81.710 | 10.960 | 24.386 |
| 0.8 | 1.990 | 23.330 | 91.931 | 11.724 | 28.137 |
| 0.9 | 1.992 | 24.467 | 101.795 | 12.283 | 31.628 |
| 1 | 1.993 | 25.514 | 111.300 | 12.802 | 35.205 |

Figure 7:
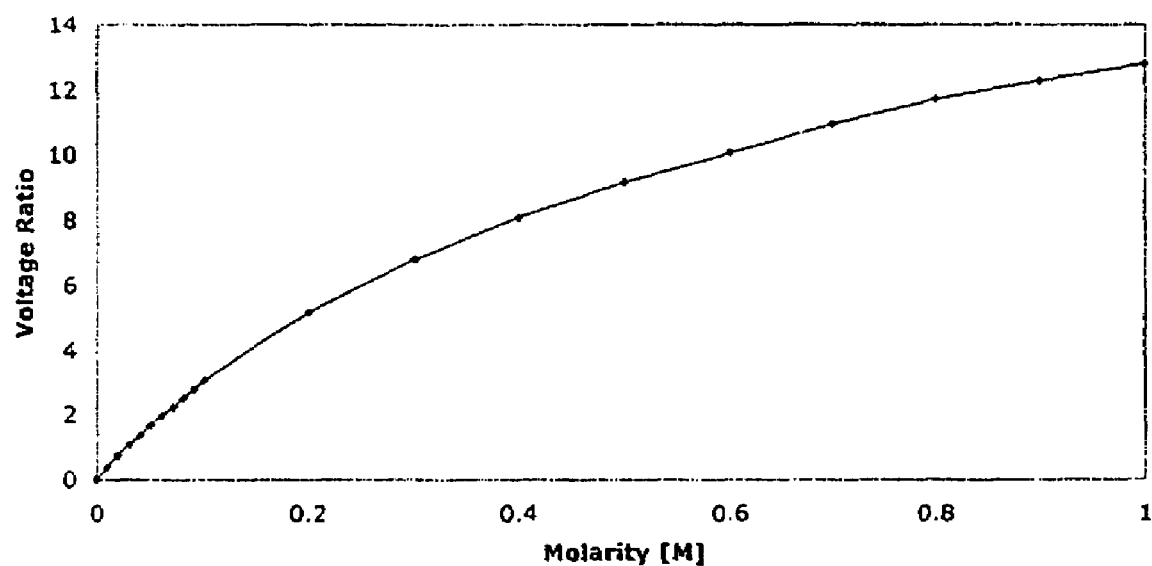
FIG. 7 shows an uncorrected plot of the voltage ratio against molarity of potassium chloride solution.
Figure 8:
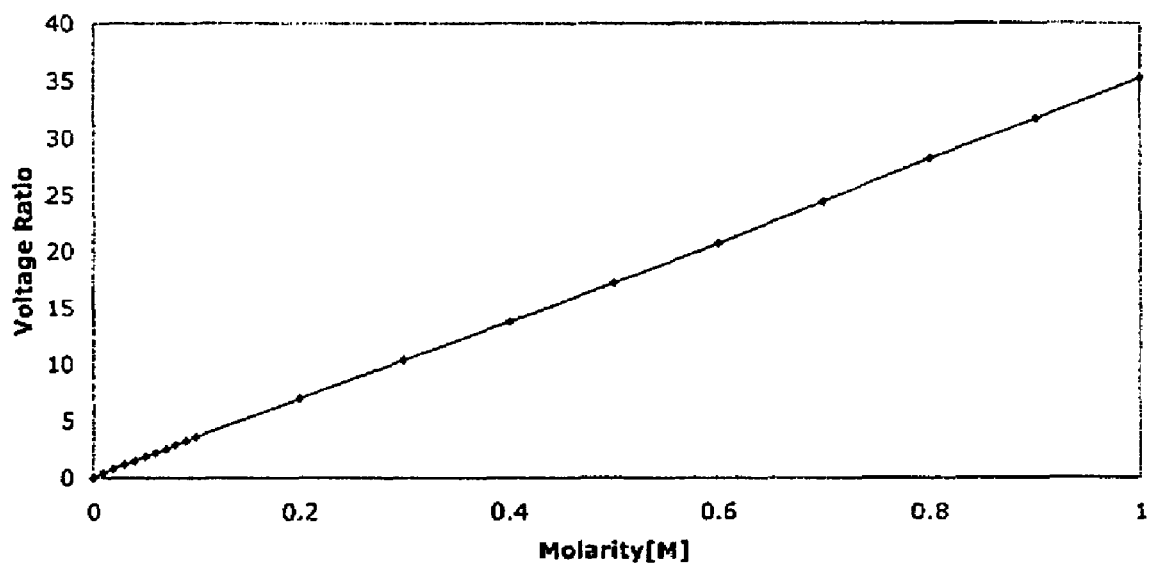
FIG. 8 shows a corrected plot of the voltage ratio against molarity of potassium chloride solution.
Figure 9:
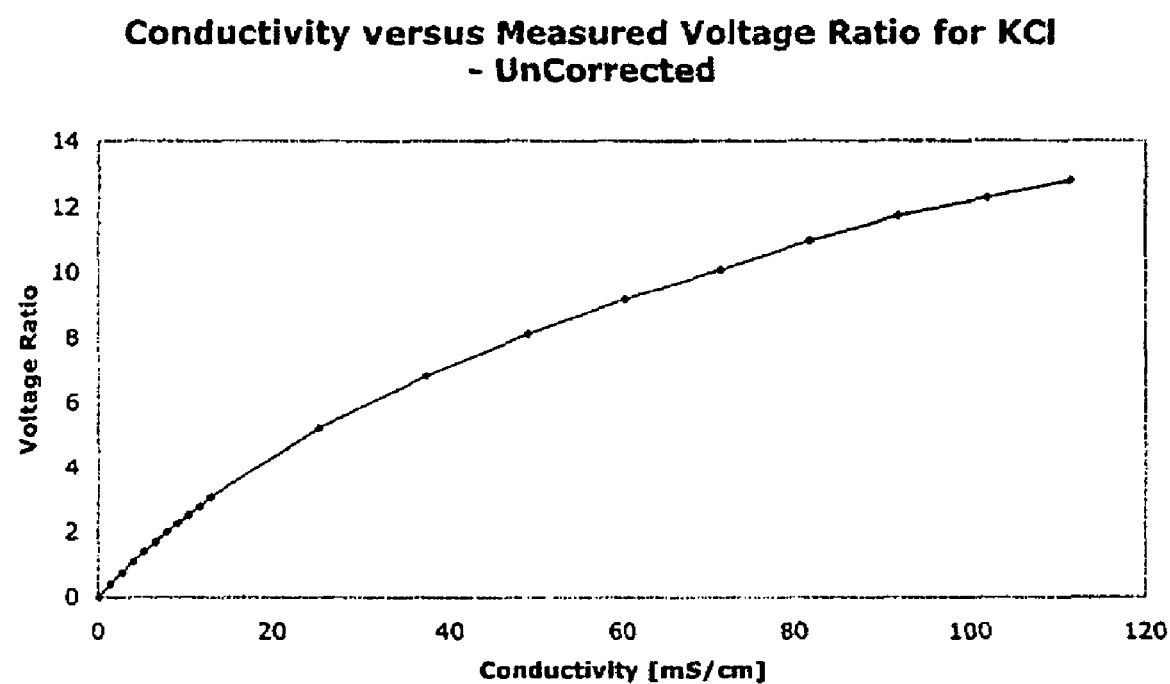
FIG. 9 shows an uncorrected plot of the voltage ratio against theoretical conductivity of potassium chloride solution.
Figure 10:
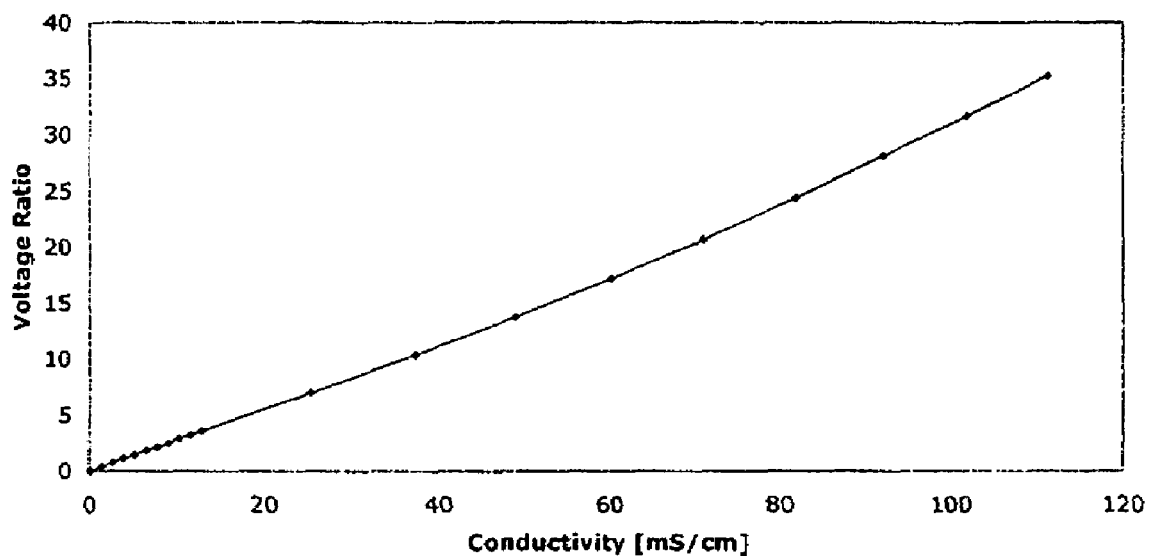
FIG. 10 shows a corrected plot of the voltage ratio against theoretical conductivity of potassium chloride solution.

Table 1 also shows the estimated conductivity of the KCl solution, which comprises an error of ±5 mS/cm. The plot of the voltage ratio $V_{ratio}$ against molarity is shown in FIG. 7. The non-linear relationship between the voltage ratio and the molarity of the solution was due to an additional resistance of 2 ohms in the second current loop 16. This was corrected for by a correction factor applied to the ratio and the corrected ratio is shown in the right hand column in Table 1. The plot of the corrected voltage ratio $V_{ratio}$ against molarity is shown in FIG. 8. The plot of the voltage ratio $V_{ratio}$ against conductivity is shown in FIG. 9. The plot of the corrected voltage ratio $V_{ratio}$ against conductivity is shown in FIG. 10.

FIGS. 7 and 8 clearly show a monotonic—and in the case of FIG. 8, an almost linear—relationship between the corrected voltage ratio and the molarity of the KCl solution in the fluid cell 4. Likewise FIGS. 9 and 10 clearly show a monotonic—and in the case of FIG. 10, almost linear—relationship between the corrected voltage ratio and the conductivity of the KCl solution in the fluid cell 4.

FIGS. 7, 8, 9 and 10 also demonstrate that the apparatus of the present invention is suitable for measuring low conductivities in materials and that it may also be employed to discriminate between very small differences in conductivity. Such a capability enables very slight changes in materials to be detected. The detection of such small changes is an indicator of changes in the characteristics of materials that may be utilised not only in food related applications, but also in other fields.

The provision of the additional transformer core 14 in the apparatus of the present invention not only enables the measurement of conductivity in low conductivity materials, but also enables the apparatus to deal with fluctuations in the energising voltage across second transformer core 12, which contributes to the stability and therefore accuracy of the measurement apparatus.

Figure 11:
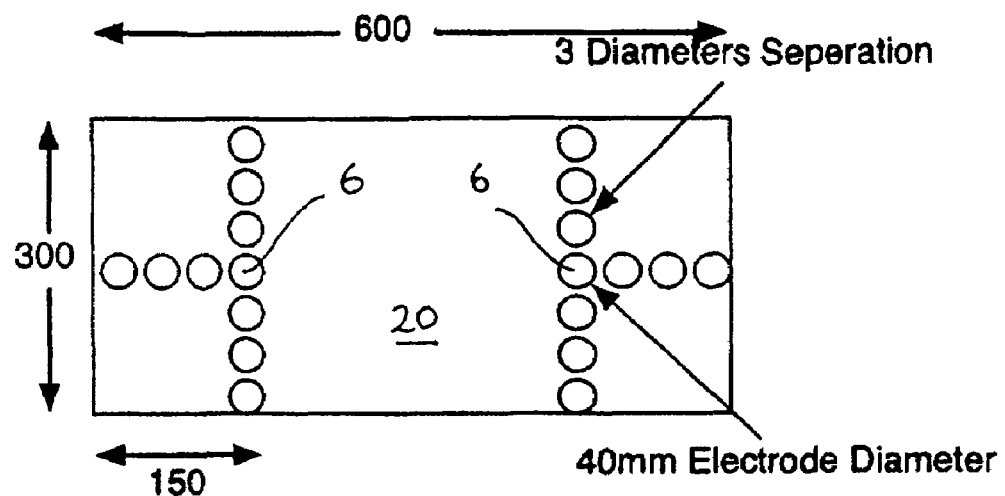
FIG. 11 shows details of the separation of the electrically conducting elements according to a preferred embodiment of the invention.
Figure 12:
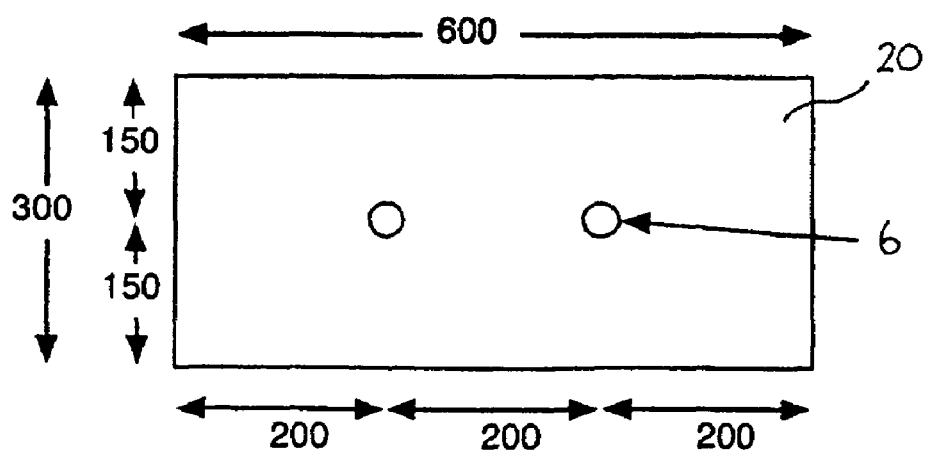
FIG. 12 shows preferred dimensions of the mounting plate in relation to the size of the electrically conducting elements.

Further details of plates 6 and mounting plate 20 will now be described with reference to FIGS. 11 and 12. Through electromagnetic modelling, the Applicant has determined that for the conductivity measurement of dairy fluids, the centre-centre separation of the circular plates 6 should be typically between about one and ten times the diameter of the plates 6, but preferably between about three and four times the diameter of the plates 6. It is envisaged that other centre-centre separations of the plates 6 will be particularly suited for the conductivity measurement of other materials. The Applicant has also determined that non-conducting mounting plate 20 should have dimensions such that its boundary is at least three times the diameter of the plates 6. Hence, as shown in FIGS. 11 and 12, for plates having a diameter of 40 mm, the separation between their centres should be about 4×40 mm−20 mm=140 mm. A mounting plate 20 having dimensions 300×600 mm satisfies the aforementioned second criterion.

Figure 13:
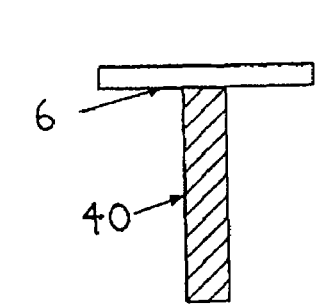
FIG. 13 shows a sectional front view of an embodiment of the electrically conducting element.
Figure 14:
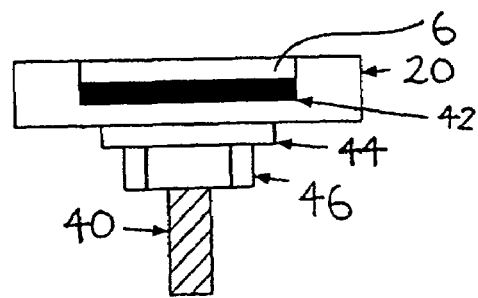
FIG. 14 shows further details of the electrically conducting element of FIG. 13.
Figure 13A:
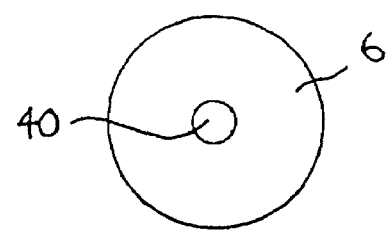
FIG. 13A shows a plan view of the electrically conducting element of FIG. 13.

With reference to FIGS. 13, 13A and 14, a preferred embodiment of the plate 6 comprises a threaded rod 40 and a stainless steel plate 6 welded to an end of the rod 40. A suitably sized plate 6 has a diameter of about 40 mm and a thickness of about 2-3 mm. Plate 6 is recessed in plastic mounting plate 20 with an elastomeric seal in the form of a rubber washer 42 disposed between the underside of plate 6 and the mounting plate 20. A second washer 44 is placed on the other side of the mounting plate 20 and secured in place with a nut 46, as shown in FIG. 14.

Figures 15, 16:
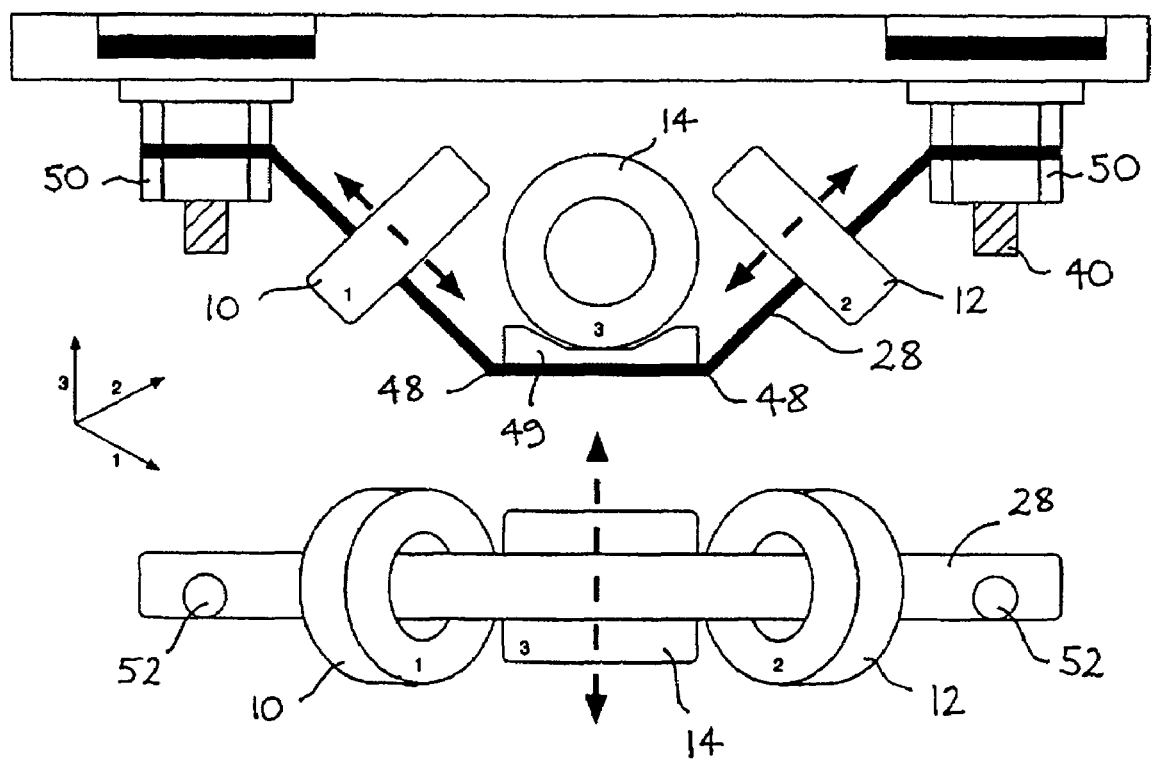
FIG. 15 is a plan view of the mounting plate and electrically conducting elements of FIG. 14 and an alternative embodiment of the loop.
FIG. 16 is a front view of the embodiment shown in FIG. 15.

Referring to FIGS. 15 and 16, the preferred mounting arrangement for the toroidal transformer cores 10, 12, 14 is such that their axes are mutually perpendicular. This minimises the magnetic cross coupling between the cores that would otherwise reduce the discrimination of the conductivity measurement. According to one embodiment, the mutually perpendicular mounting arrangement of the toroidal transformer cores is achieved with the loop 28 comprising two bends 48 at 45 degrees. The first, energising transformer core 10 and second, current sensing transformer core 12 are threaded onto the loop 28 such that they have a perpendicular orientation. The third, reference circuit sensing transformer core 14 is mechanically attached by any suitable means to the central portion of the loop 28 such that its axis is perpendicular to both transformer cores 10,12. In the embodiment shown in FIGS. 15 and 16, transformer core 14 is attached to loop 28 by means of a non-conducting mounting block 49 moulded or machined to securely hold the core 14 at right angles to the loop 28. A simple non-conducting clip or loop, such as a plastic ratchet tie, is used to hold this assembly tightly against loop 28.

Second current loop 16 is formed from a second wire 17 threading transformer cores 12 and 14 as described in previous embodiments. Loop 28 is affixed to threaded rod 40 by nuts 50 and washers. Typical internal and external diameters of the transformer cores are 18 mm and 45 mm respectively, although alternative diameter cores may be employed. In such a case, loop 28 has a thickness of about 15 mm to allow for threading of the cores 10, 12 and for shrouding (not shown) to be wrapped around the loop to protect an inner surface of the toroidal cores from scratching. Holes 52 in the loop 28 for receiving threaded rods 40 may be offset from the central axis of the loop to maintain structural strength.

Figure 17:
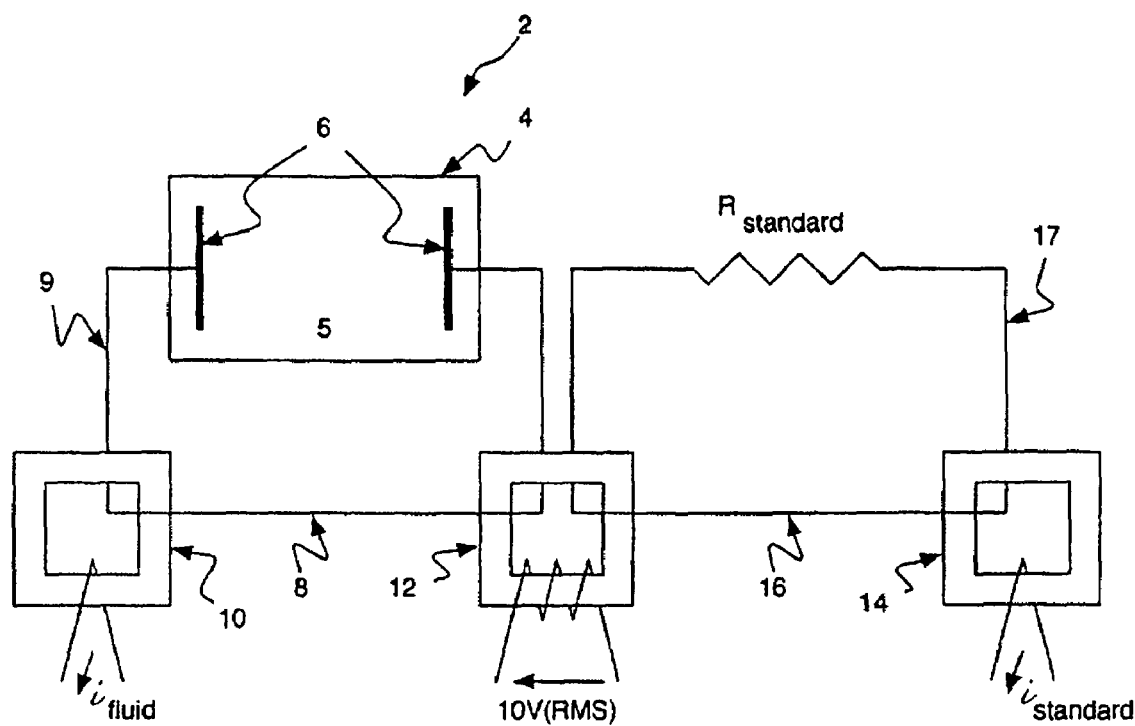
FIG. 17 shows an alternative embodiment to that shown in FIG. 1.
Figure 18:
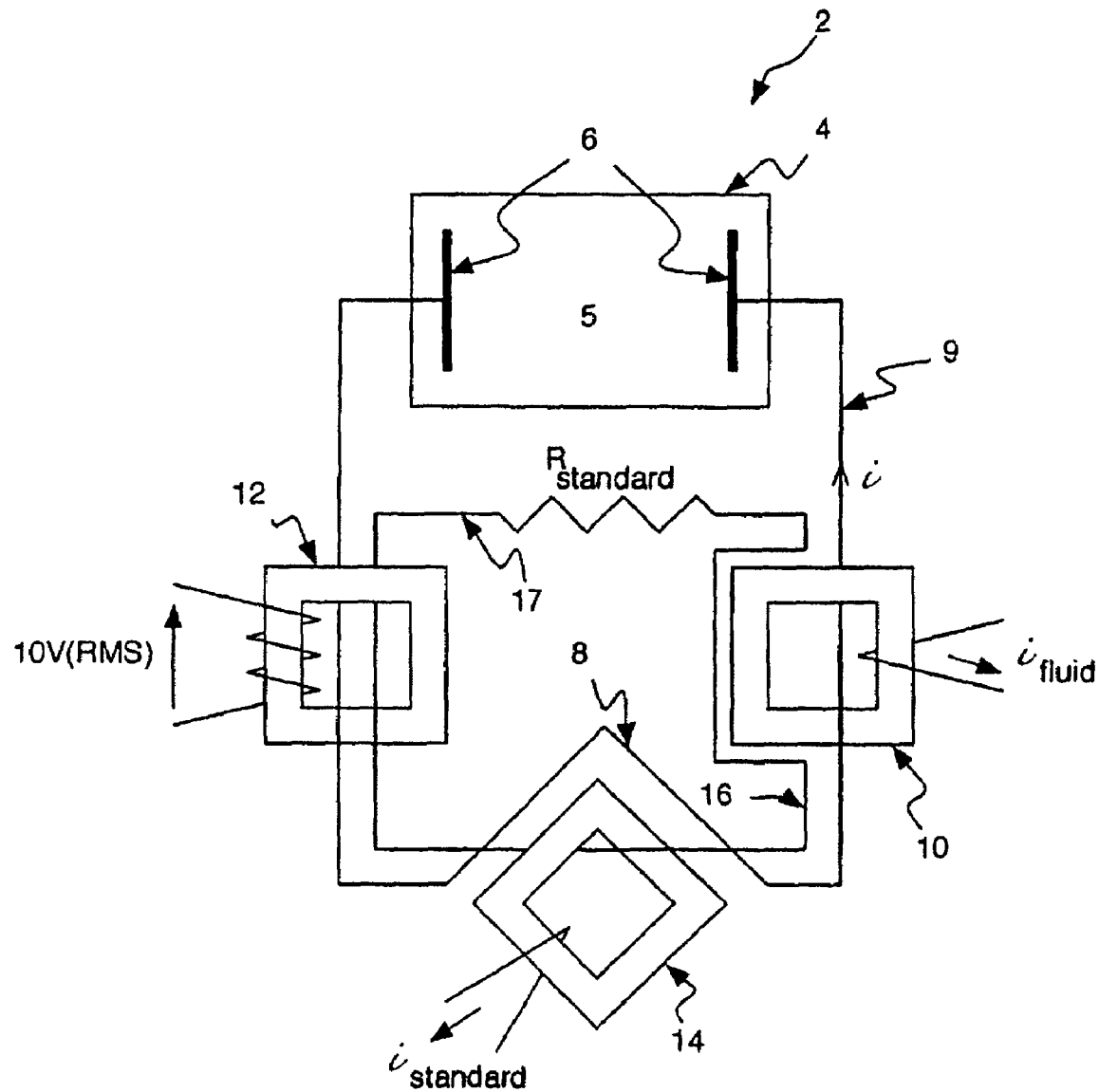
FIG. 18 shows an alternative embodiment to that shown in FIG. 2.
Figure 19:
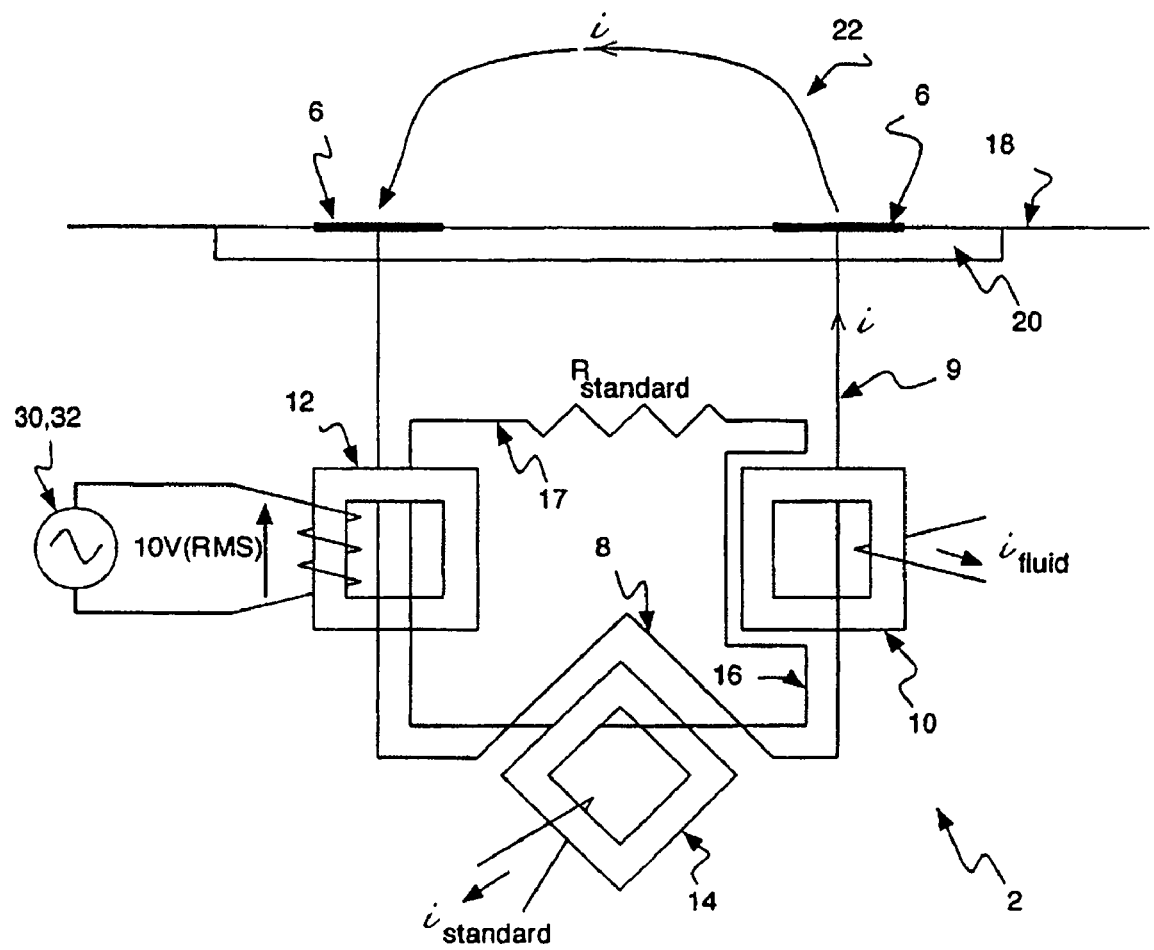
FIG. 19 shows an alternative embodiment to that shown in FIG. 3.

The Applicant has identified that current measurement can be employed as an alternative to voltage measurement and has found that current measurement is a superior method of measuring electrical conductivity. With reference to FIGS. 17-19, in both the first current loop 8 and the second current loop 16, current measurement is achieved with first and third transformer cores 10, 14 having a single secondary winding. This arrangement provides nearly a 1:1 current match with that of the current through the primary, whilst providing galvanic isolation from an ammeter (not shown) used to measure the currents i. In the embodiment shown, second transformer core has 100 windings, although this number of windings is not critical. The single winding in the first and third transformer cores maximises the current i to be measured by the ammeter.

With reference to FIGS. 20-23, another application of the present invention is the measurement of the electrical conductivity of material in pipelines. Plates 6 are mounted on insulating mounting plate 20, which occupies a proportion of a wall 19 of a pipe 18. A first current loop 8 formed by a first electrical conductor in the form of a first wire 9 couples plates 6. This arrangement creates a "half current loop" 22 between plates 6 enabling non-galvanic conductivity measurement, as described in relation to the earlier embodiments. Mounting plate 20 insulates plates 6 from each other and from the pipe wall 19. Although not shown in FIGS. 20-23, the arrangement of the measuring circuit and the transformer cores will be the same as described above and shown, for example, in FIG. 19. Non-conducting mounting plate 20 may occupy any proportion of the circumference of the pipe wall 19 depending on the diameter of the pipe 18. The plates 6 may be circumferentially or longitudinally arranged, as shown in FIGS. 20 and 21, depending on the diameter and/or geometry of the pipe 18.

Figure 23:
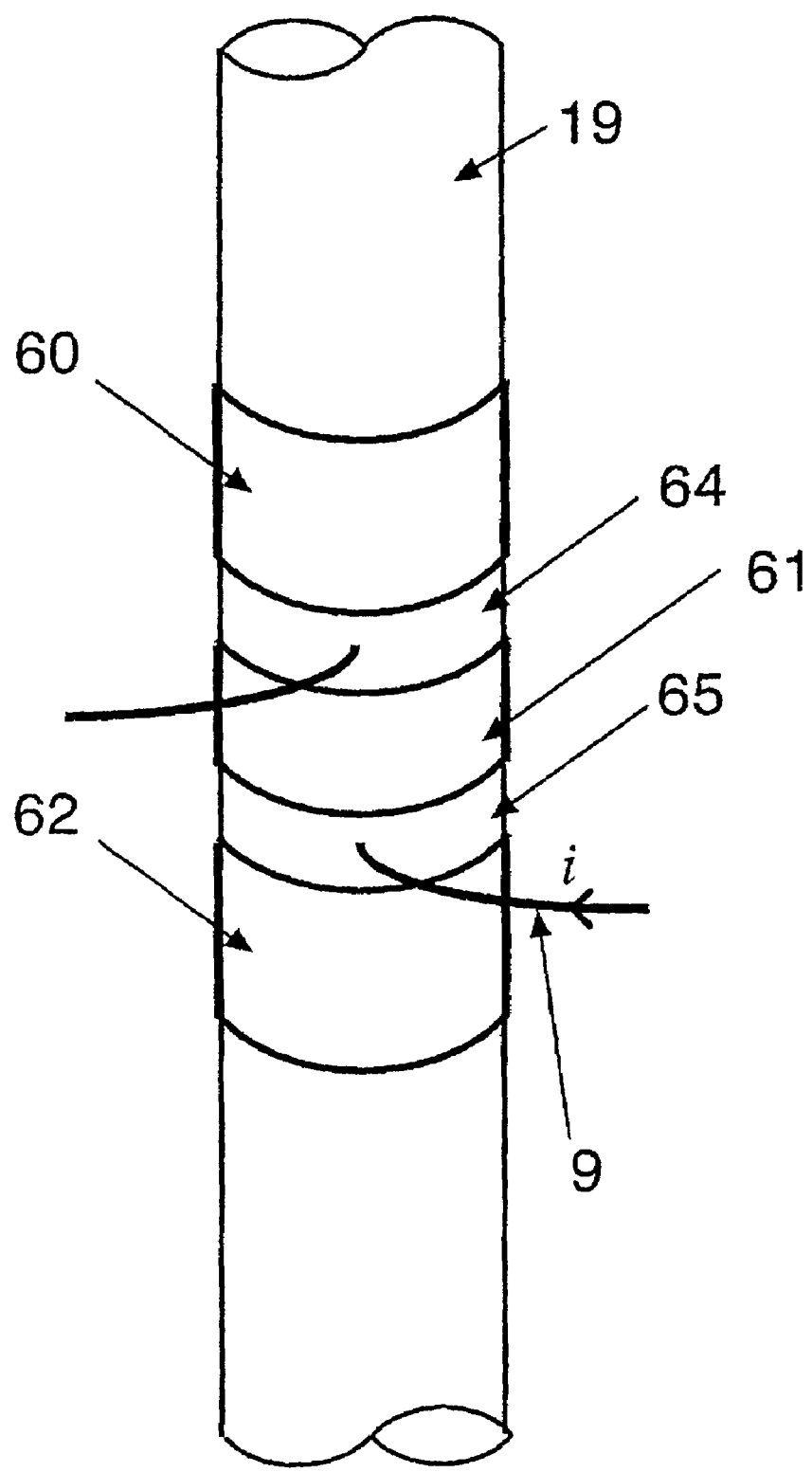
FIG. 23 is a further alternative embodiment to that shown in FIG. 20.

In an alternative embodiment, as shown in FIG. 23, mounting plate 20 is replaced by a plurality of insulating plate elements 60, 61 and 62 provided adjacent electrically conducting elements 64, 65. In this embodiment, electrically conducting elements 64, 65 are in the form of a pair of galvanically isolated rings 64, 65. Plate elements 60, 61 and 62 extend the full circumference of the pipe wall 19 as do rings 64, 65. The arrangement of the "half current loop" 22 is as described above with a first electrical conductor in the form of a first wire 9 coupling rings 64, 65.

Although the present invention has been described in relation to the measurement of electrical conductivity in a fluid cell comprising KCl solution, it will be appreciated that the present invention is also applicable to measuring the electrical conductivity in other materials in other states. Furthermore, although the apparatus and method of the present invention have been described in relation to measuring electrical conductivity in materials having low electrical conductivity, the apparatus and method described herein may also be employed to accurately measure electrical conductivity in materials having a high electrical conductivity.

Throughout the specification the aim has been to describe the invention without limiting the invention to any one embodiment or specific collection of features. Persons skilled in the relevant art may realize variations from the specific embodiments that will nonetheless fall within the scope of the invention. For example, the size, shape, area and separation of the pair of electrically conducting elements 6 and the size, shape and area of the mounting plate 20 may be varied to achieve optimum results. The particular coil winding configuration, number of windings and material employed as well as the value of the standard reference resistance may also be varied.

The invention claimed is:

1. An apparatus for measuring electrical conductivity in a material, said apparatus comprising:
   a pair of electrically conducting elements arranged for contacting the material;
   a first electrical conductor coupled to said electrically conducting elements, said first electrical conductor coupling a first transformer core and a second transformer core to form a first current loop; and
   a second electrical conductor of known resistance coupling said second transformer core and a third transformer core to form a second current loop.

2. The apparatus of claim 1, wherein said electrically conducting elements are bolts or plugs or plates.

3. The apparatus of claim 1, wherein said first, second and third transformer cores are toroidal "C", "O" or "E" transformer cores or combinations thereof.

4. The apparatus of claim 1, wherein said first, second and third transformer cores are ferrite cores, laminated cores or powdered iron cores or combinations thereof.

5. The apparatus of claim 1, further comprising
   a container for the material, and
   at least one mounting plate arranged for mounting said electrically conducting elements and attached to said container.

6. The apparatus of claim 5, wherein said second current loop is partially formed by a metal loop attached to said mounting plate and electrically coupled to said electrically conducting elements, said metal loop supporting said first and second transformer cores.

7. The apparatus of claim 6, wherein said first, second and third transformer cores are coupled to said metal loop such that axes of the transformer cores are mutually perpendicular.

8. The apparatus of claim 1, wherein a centre-to-centre separation of said electrically conducting elements is between one and ten times the diameter of said electrically conducting elements.

9. The apparatus of claim 1, wherein, for measuring electrical conductivity in dairy fluids, a centre-to-centre separation of said electrically conducting elements is between three and four times the diameter of said electrically conducting elements.

10. The apparatus of claim 5, wherein the boundary of the at least one mounting plate is at least three times the diameter of said electrically conducting elements.

11. The apparatus of claim 1, wherein said first transformer core and said third transformer core each comprises a single secondary winding.

12. The apparatus of claim 5, wherein said container is a pipe and said at least one mounting plate extends longitudinally at least partially along said pipe or circumferentially at least partially around said pipe.

13. The apparatus of claim 12, wherein said electrically conducting elements extend the circumference of said pipe.

14. The apparatus of claim 13, further comprising insulating plate elements provided adjacent said electrically conducting elements and extending the circumference of said pipe.

15. The apparatus of claim 1, additionally comprising a container for holding the material, with said elements mounted in or on said container.

16. The apparatus of claim 15, wherein said container is a fluid cell with said elements mounted within said fluid cell.

17. The apparatus of claim 15, wherein said container is a vat with said elements mounted upon a wall or walls of said vat.

18. The apparatus of claim 15, wherein said container is a pipe with said elements mounted upon a wall of said pipe.

19. A method of measuring electrical conductivity in a material, said method including the steps of:
   mounting a pair of electrically conducting elements to be in contact with said material;
   coupling said pair of electrically conducting elements with a first electrical conductor, said first electrical conductor coupling a first transformer core and a second transformer core to form a first current loop;
   coupling said second transformer core and a third transformer core with a second electrical conductor of known resistance to form a second current loop;
   measuring a voltage across said material with said first transformer core;
   monitoring an excitation voltage across said second transformer core by measuring a reference voltage across said third transformer core; and
   determining said electrical conductivity of said material from said voltage across said material, said reference voltage and said known resistance.

20. A method of measuring electrical conductivity in a material, said method including the steps of:
   mounting a pair of electrically conducting elements to be in contact with said material;
   coupling said pair of electrically conducting elements with a first electrical conductor, said first electrical conductor coupling a first transformer core and a second transformer core to form a first current loop;
   coupling said second transformer core and a third transformer core with a second electrical conductor of known resistance to form a second current loop;
   measuring a current through said material via a secondary winding of said first transformer core;
   monitoring an excitation voltage across said second transformer core by measuring a reference current through a secondary winding of said third transformer core; and
   determining said electrical conductivity of said material from said current through said material, said reference current and said known resistance.

* * * * *